United States Patent
Hoetzer et al.

(10) Patent No.: US 6,944,908 B2
(45) Date of Patent: Sep. 20, 2005

(54) DEVICE FOR KEEPING OPTICAL ELEMENTS CLEAN, IN PARTICULAR COVERS FOR SENSORS OR CAMERAS, IN MOTOR VEHICLES

(75) Inventors: Dieter Hoetzer, Schwieberdingen (DE); Dominique Breider, Echichens (CH)

(73) Assignee: Robert Bosch GmbH, Stuttgart (DE)

( * ) Notice: Subject to any disclaimer, the term of this patent is extended or adjusted under 35 U.S.C. 154(b) by 27 days.

(21) Appl. No.: 10/221,369

(22) PCT Filed: Mar. 8, 2001

(86) PCT No.: PCT/DE01/00865
§ 371 (c)(1),
(2), (4) Date: Jan. 28, 2003

(87) PCT Pub. No.: WO01/68425
PCT Pub. Date: Sep. 20, 2001

(65) Prior Publication Data
US 2003/0155001 A1 Aug. 21, 2003

(30) Foreign Application Priority Data
Mar. 11, 2000 (DE) .......................................... 100 12 004

(51) Int. Cl.[7] ................................................ B08B 7/00
(52) U.S. Cl. .................... 15/316.1; 134/94.1; 134/102.1
(58) Field of Search ............................ 134/94.1, 95.1, 134/95.2, 95.3, 99.1, 102.1, 102.2, 37; 15/250.01, 250.001, 316.1; 239/284.2, 284.1

(56) References Cited

U.S. PATENT DOCUMENTS

| 3,469,088 | A | * | 9/1969 | Coleman et al. .......... 239/284.2 |
| 4,026,468 | A | * | 5/1977 | Tinder et al. ................. 239/66 |
| 4,200,327 | A | | 4/1980 | Wepler |
| 4,363,376 | A | * | 12/1982 | Sjoberg et al. ............. 180/275 |
| 5,083,339 | A | * | 1/1992 | Bristow .................. 15/250.002 |
| 5,096,287 | A | | 3/1992 | Kakinami et al. |
| 5,385,612 | A | | 1/1995 | Li |
| 5,657,929 | A | | 8/1997 | DeWitt et al. |
| 6,166,645 | A | * | 12/2000 | Blaney ........................ 340/583 |
| 6,527,000 | B1 | * | 3/2003 | Randmae et al. .......... 134/99.1 |
| 6,527,871 | B1 | * | 3/2003 | Hanson et al. ................. 134/37 |

FOREIGN PATENT DOCUMENTS

| DE | 25 02 389 | 7/1976 |
| DE | 26 13 988 | 10/1977 |
| EP | 0 550 397 | 7/1993 |
| EP | 0 761 500 | 3/1997 |

OTHER PUBLICATIONS

*Patent Abstracts of Japan, vol. 007, No. 153 (M–226), Jul. 5, 1983 (JP 58 061047 A (Hidenori, Horiba), Apr. 11, 1983.

* cited by examiner

*Primary Examiner*—Alexander Markoff
(74) *Attorney, Agent, or Firm*—Kenyon & Kenyon

(57) ABSTRACT

The invention relates to a device for keeping optical elements clean in motor vehicles, especially sensor or camera covers. This is done according to the present invention by applying a directed stream of gas, for example a stream of air, to the transparent cover in such a way that when the cover moves relative to the surroundings no ambient atmosphere, e.g., no ambient air, reaches the surface of the cover. According to one embodiment, by using a nozzle pressurized air is blown in, producing a transverse air stream. It is also possible, using a cover, to form a buffer space in front of the cover in addition to the transverse air stream. In a further refinement, a cleaning nozzle and a heater for the cover can be provided, in order to also be able to perform cleaning when soiling has occurred during stationary operation and to remove icing at low temperatures. To this end the cleaning fluid and/or the supplied air may also be pre-heated.

16 Claims, 4 Drawing Sheets

DEVICE FOR KEEPING OPTICAL ELEMENTS CLEAN, IN PARTICULAR COVERS FOR SENSORS OR CAMERAS, IN MOTOR VEHICLES

FIELD OF THE INVENTION

The present invention is directed to a device for keeping clean optical elements in a motor vehicle, especially sensor or camera covers.

BACKGROUND INFORMATION

In increasing measure, optical sensors or cameras, which are exposed to soiling by the atmosphere, will be used in larger numbers in future motor vehicles. Even today, camera systems that help the driver in maneuvering are installed in some vehicles, in particular in trucks and buses. Such exterior cameras, or the transparent covers that cover the cameras toward the outside, are subject to soiling by dirt particles and to degradation of optical performance by ice, frost and snow. Furthermore, sensors and cameras are impaired in their optical effectiveness by deposition of liquid, especially dew or rain. This problem of soiling, and of impairment of the optical transmittance of the transparent cover, also applies to optical sensors that monitor the roadway in front of the motor vehicle, for example, in order to influence automatic regulation of illumination distance in such a way that the roadway in front of the vehicle is illuminated optimally and blinding of oncoming vehicles is prevented.

In the case of such exposed transparent covers which cover optical sensors or optical cameras toward the outside as protection against the ambient atmosphere, the problem is therefore that they must be kept in a condition which insofar as possible does not impair their optical transparency toward the outside. To this end the exposed cover must be clean or must be kept clean, and it must in general also be dry. Consequently the object of the present invention is to keep exposed transparent covers of sensors and cameras clean or if necessary to free them of dirt when they are soiled, and to dry them or keep them dry.

SUMMARY OF THE INVENTION

The device according to the present invention can be used to keep clean optical elements or components in motor vehicles, especially sensor or camera covers, by maintaining the cover of the sensors or camera in a clean and dry condition during the entire operation of the vehicle. This ensures the effectiveness of the sensor or camera.

In one aspect, the device according to the present invention includes a means of providing a directed flow of gas, e.g., of air, to the transparent cover in such a way that when the cover moves relative to the surroundings no ambient atmosphere, e.g., no ambient air, reaches the surface of the cover.

According to one particular aspect of the present invention, the cover is subjected to a transverse air stream whose direction is essentially parallel to the surface of the cover. This transverse air or transverse gas flow can be produced by at least one nozzle from which pressurized air is fed. The pressure may be constant or variable as appropriate.

According to another aspect of the present invention, a molded part is provided in front of the transparent cover and/or in front of the nozzle or nozzles, which part redirects the flow of ambient atmosphere from its incident direction perpendicular to the transparent cover in the direction of the transverse air stream, when the transparent cover is moved toward the ambient atmosphere.

Another aspect of the present invention provides for a shield projecting essentially perpendicularly from the transparent cover, which surrounds the transparent cover approximately in a ring shape and forms a buffer space in front of the surface of the cover. This structure enables the transverse air stream to be supported effectively by the formed buffer space in order to keep soil and rain away from the surface of the cover.

In another aspect of the present invention, the transparent cover may be part of a lens of the optical element, such as an optical sensor or an optical camera. Alternatively, it can be a separate element that is positioned in front of the optical element. These embodiments allow very flexible adaptation to various conditions.

The measures described above according to the present invention are especially effective when the vehicle having the transparent cover is in motion. It may occur, however, that when at rest for an extended time, the cover nevertheless is soiled by passing vehicles or by particular weather conditions. In order to also be able to clean the cover in these situations, a design of the present invention provides for at least one fluid spray nozzle for cleaning the surface of the cover.

Another design of the present invention provides for a heater, preferably an electric heater, on or in the cover. In this way ice or frost formation can be prevented or removed as quickly and effectively as possible. Alternatively or in addition, according to another aspect of the present invention a heater can be provided for the gas or air supply system and/or a heater for the cleaning fluid.

In another aspect of the present invention a controller is provided which actuates the gas or air supply, the fluid supply, if any, and/or the heater, if any, as needed.

In another aspect of the device according to the present invention, a compressor is provided to generate and produce sufficiently high gas pressure, e.g., air pressure, to produce an adequate stream of transverse gas or transverse air to blow the surface of the transparent cover free of foreign bodies and if necessary of cleaning fluid or other solid or liquid substances which impair the optical transmittance of the transparent cover.

DETAILED DESCRIPTION

Figure 1:
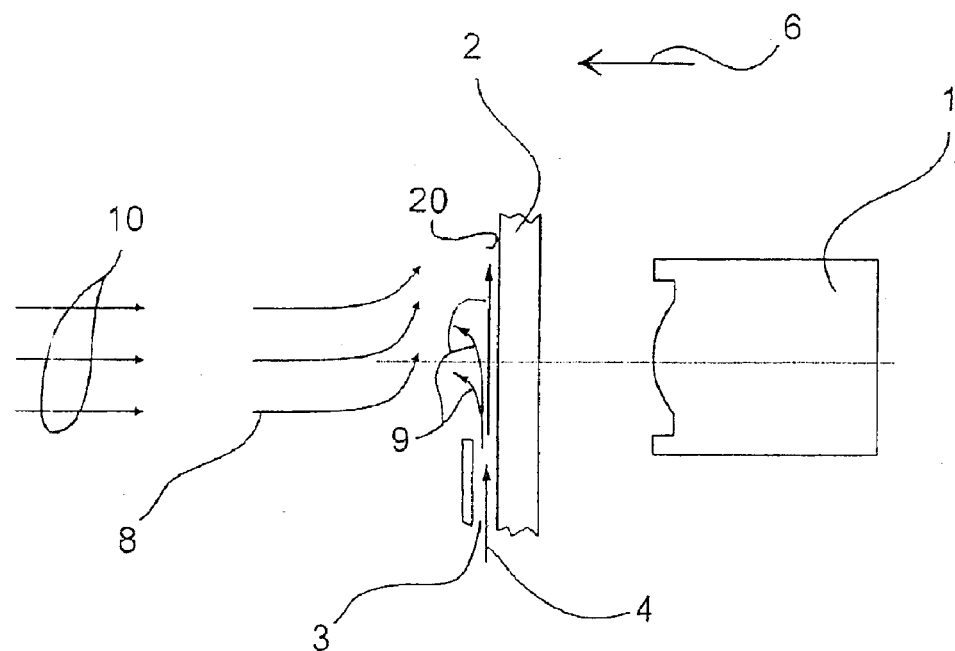
FIG. 1 shows a schematic side view of one embodiment of the device according to the present invention, having a nozzle arranged parallel to the surface of the cover.

FIG. 1 depicts a first exemplary embodiment of the present invention in schematic side view. An optical element 1, which may be an optical sensor or a camera, is sealed off from the ambient atmosphere 10 by a transparent cover 2. Optical element 1 and cover 2 move, for example when they are part of a motor vehicle, in the direction of arrow 6, so that ambient atmosphere 10 is moved toward cover 2 which may cause soiling on surface 20. According to the present invention, transparent cover 2 is acted on by a directed gas stream, especially an air stream, in such a way that when cover 2 moves together with optical element 1 in the direction of arrow 6, i.e. relative to the surroundings, no ambient atmosphere 10 reaches surface 20 of cover 2 directly. According to the embodiment in FIG. 1, in the vicinity of cover 2 at least one nozzle 3 is provided for that purpose, through which a gas or air stream 4 is fed with constant or variable pressure. The direction of nozzle 3 and of air stream 4 is chosen so that a transverse air stream 9 results, which flows essentially parallel to surface 20 of cover 2 and also redirects the inflowing ambient air, illustrated by reference symbol 8 and the corresponding arrows, in the direction of transverse air steam 9. In this way transparent cover 2 is effectively kept free of dirty and soiling ambient atmosphere 10, so that the optical properties of optical element 1 are not impaired by soiling or moistening from rain or ice of transparent cover 2.

Figure 2:
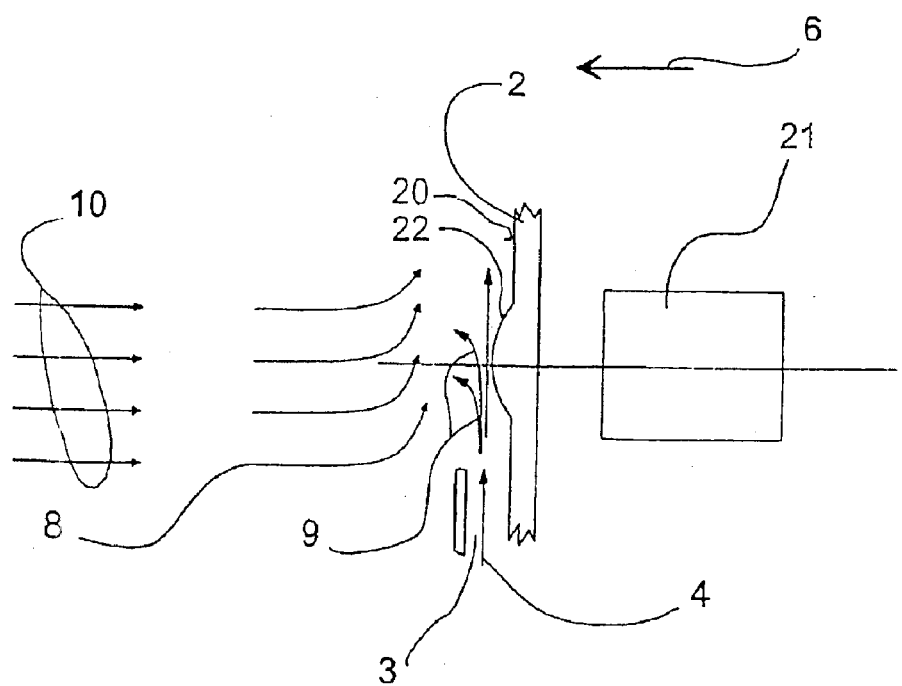
FIG. 2 shows an arrangement similar to that in FIG. 1, in which the cover is in the shape of a lens and the sensor behind it has no such lens.

The embodiment portrayed in FIG. 2 differs from that in FIG. 1, in that sensor 21 is designed without a lens shape in the direction of cover 2, and the corresponding lens has been shifted to cover 2. Hence, this design results in a lens-shaped surface 22 on transparent cover 2 of FIG. 2. In terms of effect, the invention here is otherwise exactly like the embodiment portrayed in FIG. 1.

Figure 3:
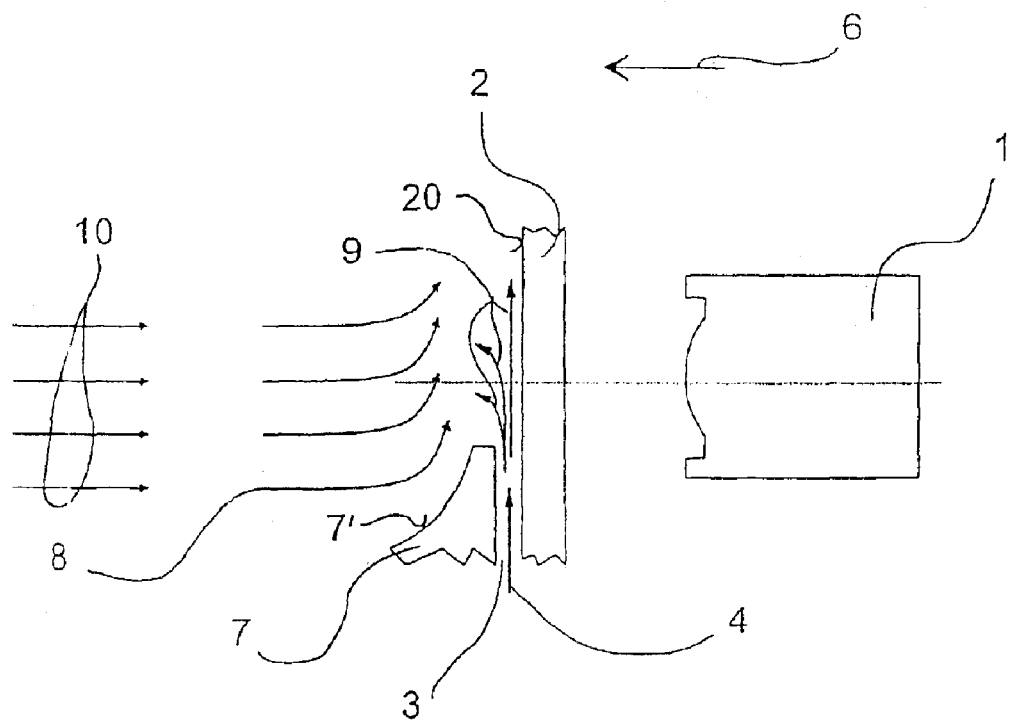
FIG. 3 shows a schematic side view of an arrangement similar to that in FIG. 1, but with an additional molded part that supports the transverse flow produced by the nozzle when the cover moves.
Figure 4:
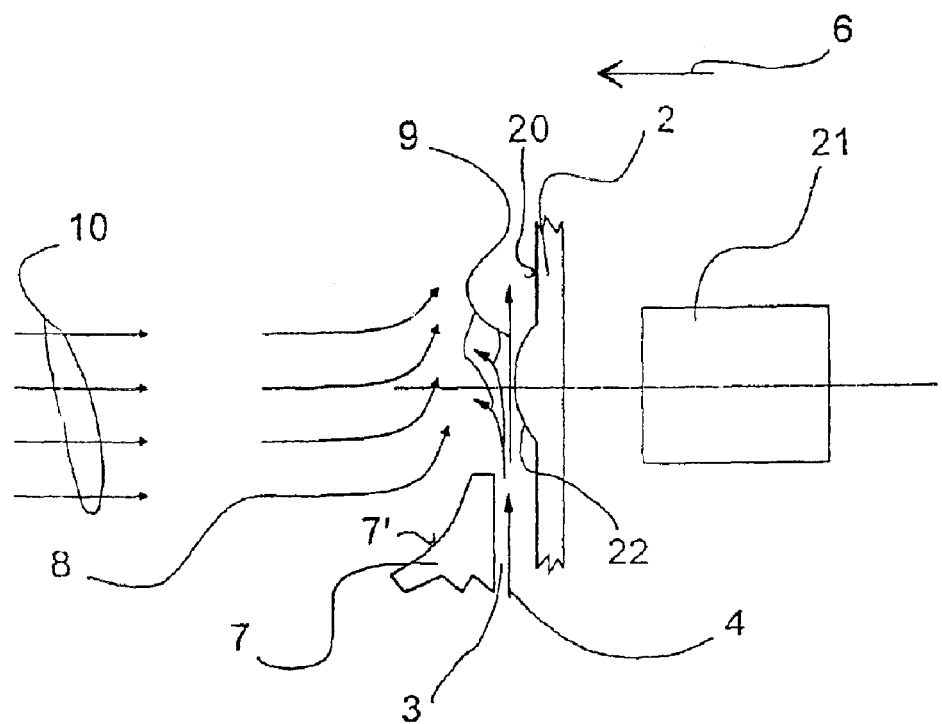
FIG. 4 shows an arrangement similar to that in FIG. 3, in which the cover is in the form of a lens and the sensor behind it has no such lens.

The embodiment portrayed in FIG. 3 corresponds essentially to that in FIG. 1, and the one in FIG. 4 to that in FIG. 2, but here an additional molded part 7 is provided to support air stream 4 produced by nozzle 3, having a surface 7' that redirects air stream 8, which is flowing perpendicular to cover 2, in the direction of air stream 4. When transparent cover 2 together with optical element 1 moves in the direction of arrow 6 relative to ambient atmosphere 10, air stream 4 produced by nozzle 3 is effectively relieved by this molded part 7, which is attached in front of transparent cover 2 and in front of nozzle or nozzles 3, so that the pressure of the pressurized air that must be fed through nozzle 3 may be reduced. The pressure may also be varied depending on the relative speed between cover 2 and ambient atmosphere 10. In the embodiment according to FIG. 4, cover 2 is furnished with a lens 22 corresponding to the embodiment in FIG. 2, and optical element 21 has no lens part in the direction of cover 2.

Figure 5:
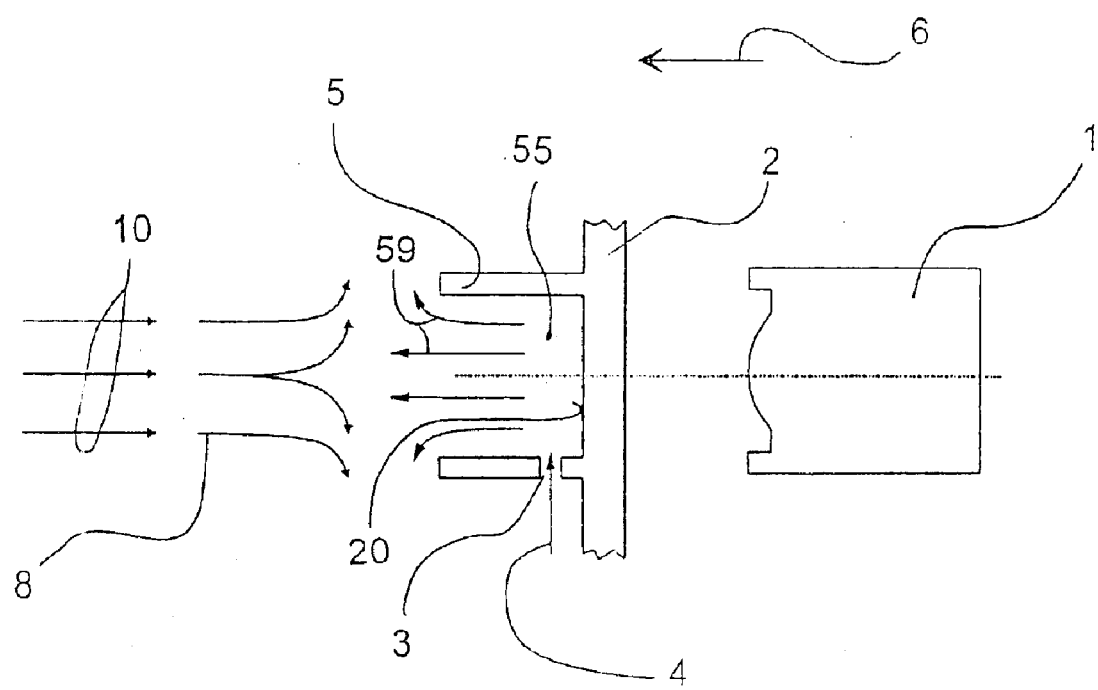
FIG. 5 shows another embodiment of the arrangement according to the present invention in schematic side view, having a shield of essentially ring-shaped design projecting from the cover, at the base of which the transverse stream nozzle is positioned near the surface of the cover.

In the embodiment according to FIG. 5, cover 2 is provided with an essentially ring-shaped shield 5 in the area in front of optical element 1. This shield 5 surrounds the external surface that is exposed to soiling by ambient atmosphere 10 in a ring shape, and because of its shape forms a buffer space 55 in front of surface 20 of transparent cover 2. Pressurized air entering through nozzle 3, together with air stream 4, produces transverse air stream 9, although with the provision in this case that the air does not flow away quite transversely but is forced out toward the front and supports the effect of buffer space 55 in such a way that a counter-airstream 59 is produced which redirects the oncoming ambient air according to arrows 8.

That too effectively prevents ambient atmosphere 10 from being able to reach surface 20 of cover 2. In FIG. 5 a nozzle 3 is shown near surface 20 of cover 2. It is clear that several nozzles may be distributed around buffer space 59 in ring-shaped cover 5 in order to build up an effective counter-cushion of air or gas ahead of oncoming ambient atmosphere 10. Shield 5 may be designed as one piece with cover 2, or may be connected with the cover in some known and suitable manner.

Figure 6:
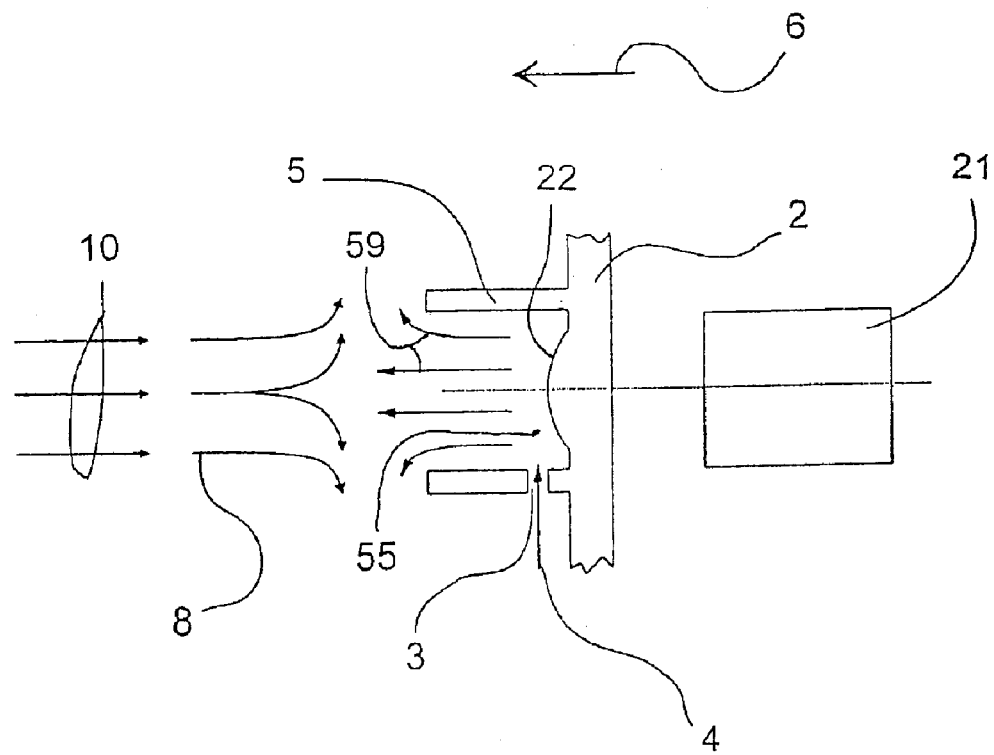
FIG. 6 shows an arrangement similar to that in FIG. 5, in which the cover is in the form of a lens and the sensor behind it has no such lens.

Another embodiment of the present invention is illustrated in FIG. 6 which corresponds in its essentials to that in FIG. 5. In this embodiment, however, sensor 21 is designed without a lens shape in the direction of cover 2, and the corresponding lens has been shifted to cover 2. Hence this design results in a lens-shaped surface 22 on transparent cover 2 of FIG. 4. In terms of effect, the invention here is otherwise exactly like that illustrated in FIG. 5, having buffer space 55 in front of lens-shaped surface 22 with cover 2.

The embodiments in FIGS. 2, 4 and 6 show that transparent cover 2 is equipped with a lens 22, so that optical element 21 itself is without a lens. In the embodiments according to FIGS. 1, 3 and 5 cover 2 is a special part that is positioned in front of the lens as a separate part, optical element 1 itself then being equipped with a lens or the like. The lens-shaped part 22 of surface 20 of the transparent cover, as illustrated in FIGS. 2, 4 and 6, may be any optical element, such as a lens, a diffractive optical system, a holographic optical system, facets, prisms or the like. This also applies analogously to the similarly designed surface of element 1 in FIGS. 1, 3 and 5.

Figure 7:
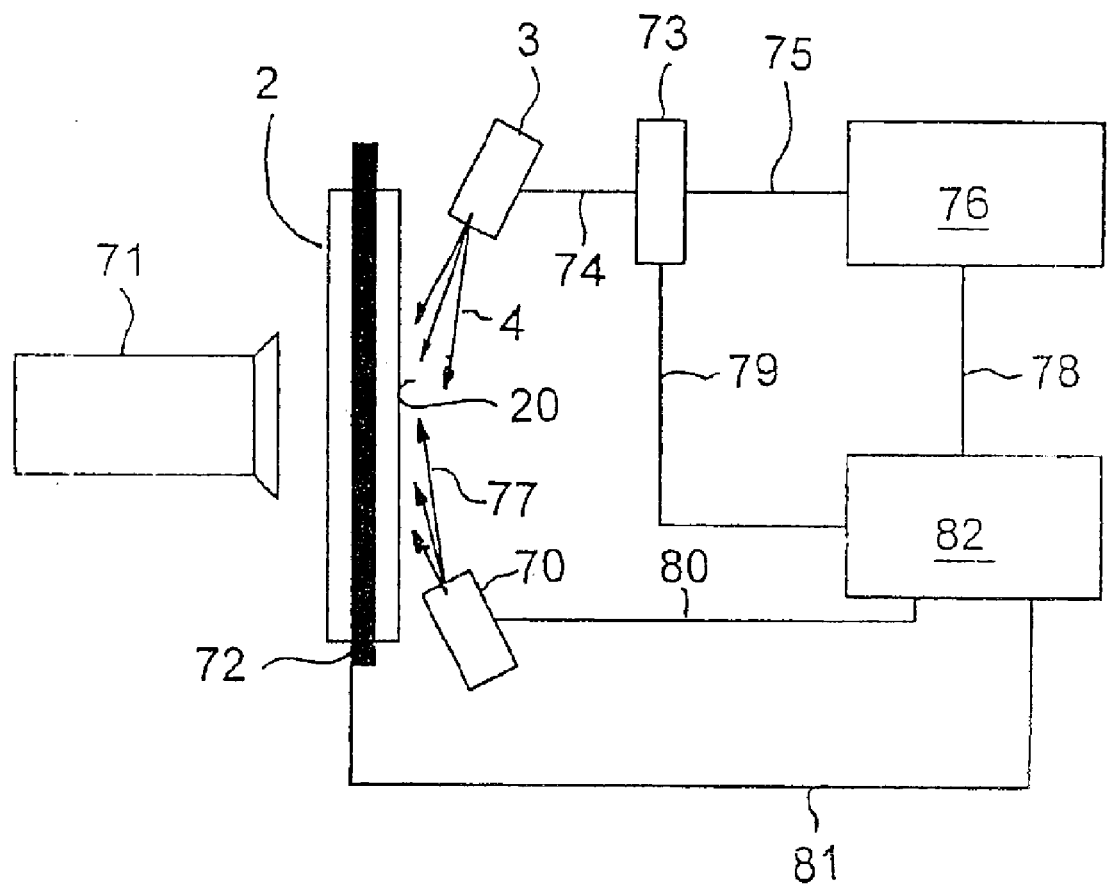
FIG. 7 shows in schematic side view and block representation the arrangement of a heatable cover of a sensor or a camera and the controller, along with a fluid supply nozzle and air nozzle.

The schematic representation in FIG. 7 illustrates another embodiment of the present invention. As the optical element here, for example, a camera 71 may record the observable surroundings through a transparent cover 2, which may include a pane of glass. In addition to air nozzle 3 producing transverse air stream 4, a fluid spray nozzle 70 is also provided here, which uses cleaning fluid that may be sprayed in the direction of arrows 77 onto surface 20 of cover 2 in order to clean the cover. To prevent icing, a heating layer 72 for example may also be built into cover 2 to thaw the ice, the interfering drops of liquid then being blown away by air nozzle 3, thus drying surface 20. Heating layer 72 may of course also be provided on transparent cover 2, in particular on its surface. This heating layer, or in more general terms heater 72, is operated electrically, for example. To blow surface 20 free of drops of liquid, pressurized air is fed to nozzle 3 through a line 74 from a valve 73, which in turn is connected to a compressor 76 through a line 75. The container for water or cleaning fluid to supply fluid nozzle 70 is not shown. A controller 82 is provided, which is connected through control line 78 to compressor 76, through control line 79 to valve 73, through control line 80 to fluid supply nozzle 70 and through control line 81 to heater 72.

Alternatively to heater 72, which may be provided on or in transparent layer 2 as a layer, or if appropriate in addition to it, according to another example embodiment of the present invention a heater may be provided for the gas or air supply system and/or a heater for the cleaning fluid. This heater for heating supplied gas or air and sprayed-on cleaning fluid is not portrayed in the figures.

In addition to the advantageous production of transverse air stream 4 corresponding to the present invention, in this embodiment according to FIG. 7 there is the additional possibility that because cleaning fluid is being fed through nozzle 70, surface 20 of cover 2 may still be cleaned in the event that it has been soiled, for example when the vehicle is stopped. The water deposits which then remain are removed by the pressurized air fed through nozzle 3. At cold temperatures cover 2 may ice up. In order to provide a clear view for camera 71 used as an optical element in this situation as well, cover 2 is warmed up by electrical heater 72 and/or by the pre-heated cleaning fluid and/or pressurized air, so that icing disappears. The drops of liquid which develop during thawing are removed by means of air stream 4 supplied with air nozzle 3 and the transverse air stream thus produced.

Using controller 82, in the invention the supply of gas or air and the supply of liquid to cleaning nozzle 70, if any, as well as switching heater 72 on and off, are regulated according to need. Compressor 76 is used to generate and produce adequately high gas or air pressure, so that a sufficiently strong transverse gas or air stream is available to blow surface 20 or 22 of cover 2 clear. In that way transparent cover 2 is effectively kept or blown clear of foreign bodies and of cleaning fluid, if any, as well as of other solid or liquid substances which impair the optical transmittance of transparent cover 2, and is dried.

In summary, the present invention provides a device that keeps the transparent cover of optical lements, especially sensors or cameras, clean, or is capable of cleaning them, so that the optical sensivity of the covered elements is not impaired.

What is claimed is:

1. A device for keeping clean an optical element in a motor vehicle, comprising:

a cover for the optical element;

a means for delivering a stream of gas under pressure to the cover of the optical element, the means for delivering a stream of gas under pressure adapted to deliver a stream of gas to the cover to prevent ambient atmosphere from reaching a surface of the cover when the cover moves toward ambient atmosphere, the stream of gas being directed substantially parallel to the surface of the cover;

a means for at least one of monitoring and regulating the pressure of the stream of gas; and a molded part positioned in front of at least one of the cover and the means for delivering the stream of gas, wherein the molded part redirects a flow of ambient atmosphere impacting the cover essentially perpendicularly, in a direction of the stream of gas flowing substantially parallel to the surface of the cover, when the cover is moved in a direction of ambient atmosphere.

2. The device of claim 1, wherein the cover is transparent, and wherein the cover forms an optical surface of the optical element.

3. The device of claim 1, wherein the optical component is one of an optical sensor and an optical camera.

4. The device of claim 1, wherein the stream of gas is a stream of air.

5. The device of claim 1, wherein the cover is transparent.

6. The device of claim 5, wherein the means for delivering the pressurized stream of gas includes at least one nozzle.

7. The device of claim 1, wherein the cover is transparent, and wherein a shield is provided projecting essentially perpendicularly from the transparent cover, the shield enclosing the transparent cover in a ring shape and forming a buffer space in front of a surface of the transparent cover.

8. The device of claim 1, wherein the cover is transparent, and the transparent cover is a separate component placed between the optical element and the ambient atmosphere.

9. The device of claim 8, wherein the optical element is one of an optical camera and an optical sensor.

10. The device of claim 1, wherein the cover is transparent, the device further comprising at least one fluid spray nozzle for cleaning the surface of the transparent cover.

11. The device of claim 10, further comprising a heater positioned one of on and in the transparent cover.

12. The device of claim 1, wherein the cover is transparent, the device further comprising a heater positioned one of on and in the transparent cover.

13. The device of claim 12, wherein the heater is an electrical heater.

14. The device of claim 1, further comprising a heater for the stream of gas.

15. The device of claim 1, wherein the cover is transparent, the device further comprising:

at least one fluid spray nozzle for cleaning a surface of the transparent cover with a cleaning fluid;

a heater positioned one of on and in the transparent cover; and a controller to actuate at least one of the gas supply, the fluid supply, and the heater according to demand.

16. The device of claim 12, further comprising a compressor to generate adequately high gas pressure to produce a sufficient stream of gas to blow the surface of the transparent cover clear of at least one of liquid and solid matter impairing optical transmittance of the transparent cover.

* * * * *